US006756231B1

(12) United States Patent
Nagano et al.

(10) Patent No.: US 6,756,231 B1
(45) Date of Patent: Jun. 29, 2004

(54) DIAMINORHODAMINE DERIVATIVE

(75) Inventors: Tetsuo Nagano, 28-15, Amanuma 1-chome, Suginami-ku, Tokyo 167-0032 (JP); Hirotatsu Kojima, Tokyo (JP); Kazuya Kikuchi, Kanagawa (JP)

(73) Assignees: Daiichi Pure Chemicals Co., Ltd., Tokyo (JP); Tetsuo Nagano, Tokyo (JP)

( * ) Notice: Subject to any disclaimer, the term of this patent is extended or adjusted under 35 U.S.C. 154(b) by 0 days.

(21) Appl. No.: 09/641,350

(22) Filed: Aug. 18, 2000

(51) Int. Cl.[7] ........................ G01N 33/00; C07D 493/00
(52) U.S. Cl. ........................ 436/116; 436/106; 436/164; 436/172; 549/265; 549/227
(58) Field of Search ................................. 436/106, 116, 436/164, 172; 549/265, 227

(56) References Cited

U.S. PATENT DOCUMENTS 5,874,590 A    2/1999  Nagano et al.
6,201,134 B1 *  3/2001  Nagano et al. ............ 549/227
6,469,051 B2 * 10/2002  Nagano et al. ............ 514/453

FOREIGN PATENT DOCUMENTS

JP    9-043153      2/1997
JP    10226688     8/1998
WO    99/01447      1/1999
WO    01/63265   *  8/2001

OTHER PUBLICATIONS

Analytical Chemistry. "Bioimaging of Nitric Oxide with Fluorescent Indicators Based on the Rhodamine Chromophore". Kojima et al. Mar. 2001.*
English Language Abstract of JP 9–043153.
English Language Abstract of JP 10–226688.
Chemistry Today [Gendai Kagaku], Apr., pp. 25–29 (1994), Japanese Language.
Palmer et al., *Nature*, vol. 327, pp. 524–526 (1987).
Kelm et al., *Circulation Research*, vol. 66, No. 6, pp. 1561–1575 (1990).
Shibuki, *Neuroscience Research* 9, pp. 69–76 (1990).
Malinski et al., *Nature*, vol. 358, pp. 676–678 (1992).
Green et al., *Analytical Biochemistry*, vol. 126, pp. 131–138 (1982).
"Approaches From The Newest Medicine [Saishin Igaku Kara No Approach] 12, NO", Ed. by Noboru Toda, pp. 42–52, Japanese Language.
Archer, *The FASEB Journal*, vol. 7, pp. 349–360 (1993).
Stainton, Analytical Chemistry, vol. 46, No. 11, p. 1616, (1974.
Sawicki et al., *Microchemical Journal*, vol. 16, pp. 657–672 (1971).
Wiersma, *Analytical Letters*, vol. 3, No. 3, pp. 123–132 (1970).
Damiani, *Talanta*, vol. 33, No. 8, pp. 649–652 (1986).

Misko, *Analytical Biochemistry*, 214, pp. 11–16 (1993).
*Dojin News*, No. 74, p. 18 (1995), Japanese Language.
Sawicki, *Analytical Letters*, 4, (11), pp. 761–775 (1971).
Maeda et al., *Journal of Leukocyte Biology*, vol. 56, pp. 588–592 (1994).
Akaike et al., *Biochemistry*, vol. 32, pp. 827–832 (1993).
Tokyo Chemical Industry Co., Ltd., Organic Chemicals Catalog, 32, (1994).
Kikuchi et al., *Biol. Pharm. Bull.*, 19, (4), pp. 649–651 (1996).
Fleming et al., *Circulation Research*, vol. 74, No. 6 pp. 1220–1226 (1994).
Abstracts of Papers, Part 1, 218th ACS National Meeting, American Chemical Society, Aug. 22–26 (1999).
Kojima et al., *Angew Chem. Int. Ed.*, 38, No. 21 pp. 3209–3212 (1999).
Kojima et al., *Tetrahedron Letters*, 41, pp. 69–72 (2000).

* cited by examiner

*Primary Examiner*—Jill Warden
*Assistant Examiner*—Latoya Cross
(74) *Attorney, Agent, or Firm*—Greenblum & Bernstein, P.L.C.

(57) ABSTRACT

A compound represented by the following formula (I) or (II):

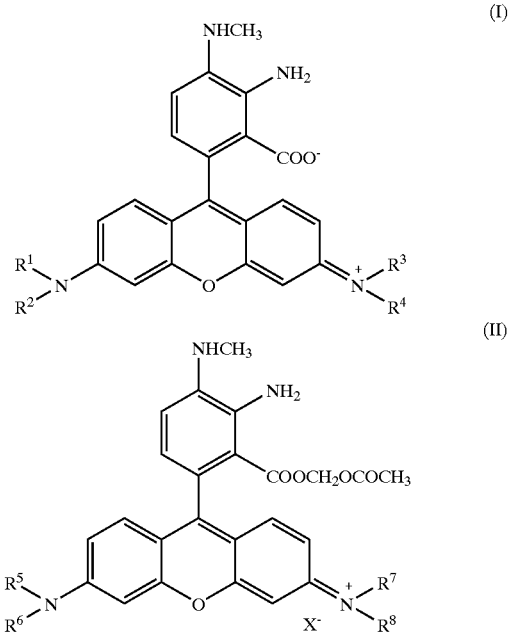

wherein, in the formula (I), $R^1$, $R^2$, $R^3$, and $R^4$ independently represent methyl group or ethyl group; and in the formula (II), $R^5$, $R^6$, $R^7$, and $R^8$ independently represent methyl group or ethyl group and $X^-$ represents an anion, and a reagent for measurement of nitric oxide which comprises said compound.

8 Claims, 3 Drawing Sheets

DIAMINORHODAMINE DERIVATIVE

TECHNICAL FILED

The present invention relates to a rhodamine derivative useful as a reagent for measurement of nitric oxide, and a reagent for nitric oxide measurement that comprises said compound.

BACKGROUND ART

Nitric oxide (NO) is an unstable radical species of a short life, and has been elucidated to have important functions as a physiological active substance in a living body (Chemistry Today [Gendai Kagakul], April, 1994, Special Edition; Pharmacia, May, 1997, Special Edition). Methods for measuring nitric oxide are roughly classified into indirect methods, which measure $NO_2^-$ and $NO_3^-$ as oxidative degradation products of nitric oxide, and methods based on direct measurement of nitric oxide. The direct methods have been desired from viewpoints of detection and quantification of nitric oxide under physiological conditions. However, any specific and highly sensitive detection method that can be applied to in vitro systems has not been developed so far.

As typical methods, there are known, for example, the chemiluminescence method utilizing the luminescence generated by ozone oxidation of NO radicals (Palmer R. M., et al., Nature, 327, pp.524–526, 1987), a method determining absorption spectrum of metHb which is produced by oxidation of oxyhemoglobin ($O_2Hb$) (Kelm M., et al., Circ. Res. 66, pp.1561–1575, 1990), a method for quantification utilizing the flow of electric current produced in oxidation when electrodes are placed in a tissue (Shibuki K., Neurosci. Res. 9, pp.69–76, 1990; Malinski, and T., Nature, 358, pp.676–678, 1982), the Griess reaction method (Green L. C., et al., Anal. Biochem., 126, pp.131–138, 1992) and so forth (as reviews, see, "Approaches From The Newest Medicine [Saishin Igaku Kara No Approach] 12, NO", Ed. by Noboru Toda, pp.42–52, Section 3, Tetsuo Nagano, Measuring Method of NO, published by Medical View Co., Ltd; Archer, S., FASEB J., 7, pp.349–360,1993).

The Griess reaction method achieves the detection by using azo coupling of a diazonium salt compound and naphthylethylenediamine in the presence of $NO_2^-$ that is produced by oxidation of a nitric oxide radical. Although this method does not achieve direct measurement of nitric oxide radicals, the method is advantageous since it requires no special apparatuses or techniques. Moreover, this method also has a characteristic feature that nitric oxide-related metabolites can be quantified, since $NO_3^-$ can be measured after being reduced to $NO_2^-$ with cadmium (Stainton M. P., Anal. Chem., 46, p.1616, 1974; Green L. C., et al., Anal. Biochem., 126, pp.131–138, 1982) or hydrazine (Sawicki, C. R. and Scaringelli, F. P., Microchem. J., 16, pp.657–672, 1971).

2,3-Diaminonaphthalene is known as a reagent for measuring nitric oxide by detecting $NO_2^-$ in a similar manner to the Griess reaction method. This reagent reacts with $NO_2^-$ under an acidic condition to form a fluorescent adduct, naphthalenetriazole (chemical name: 1-[H]-naphtho[2,3-d] triazole, Wiersma J. H., Anal. Lett., 3, pp.123–132, 1970). The conditions for the reaction of 2,3-diaminonaphthalene with $NO_2^-$ have been studied in detail. The reaction proceeds most quickly at pH 2 or lower and completes in approximately 5 minutes at room temperature (Wiersma J. H., Anal. Lett., 3, pp. 123–132, 1970; Sawicki, C. R., Anal. Lett., 4, pp.761–775, 1971). The generated adduct emits fluorescence most efficiently at pH 10 or higher (Damiani, P. and Burini, G., Talanta, 8, pp.649–652, 1986).

The method for measuring nitric oxide using the 2,3-diaminonaphthalene is characterized in that a detection limit is about several tens nanomoles and sensitivity is 50 to 100 times higher than that of the Griess reaction method (Misko, T. P., Anal. Biochem. 214, pp.11–16, 1993). This method is also excellent since it can be carried out conveniently without need of any special apparatuses or techniques (as a review of the above methods, see, DOJIN News, No. 74, Information Measurement Reagents for NO: 2,3-Diaminonaphthalene, published by Dojindo Laboratories Co., Ltd., 1995). However, this method does not utilizes nitric oxide, per se, but its oxidation product $NO_2^-$ as the reaction species, and accordingly, the method is rather indirect as compared to the direct methods for measuring nitric oxide. In addition, since the reaction of 2,3-diaminonaphthalene and $NO_2^-$ is performed under a strongly acidic condition (pH 2 or lower), it has a problem that the method cannot be used for detection and quantification of nitric oxide under a physiological condition.

The inventors of the present invention conducted researches to provide means for direct measurement of nitric oxide with high sensitivity under a physiological condition. As a result, the inventors found that 2,3-diaminonaphthalene or a derivative thereof efficiently reacts with nitric oxide to give fluorescent naphthalenetriazole or its derivative, even under a neutral condition, in the presence of an oxygen source such as dissolved oxygen or oxide compounds (for example, PTIO and its derivatives such as carboxy-PTIO). Moreover, the inventors also found that a method for measuring nitric oxide employing this reaction gave extremely high detection sensitivity and achieved accurate quantification of a trace amount of nitric oxide (see, the specification of Japanese Patent Unexamined Publication (Kokai) No. 9-043153/1997).

However, the aforementioned method utilizing 2,3-diaminonaphthalene needs irradiation by excitation light of a short wavelength such as about 370 to 390 nm for the detection of fluorescence, and accordingly, cells and tissues in a measurement system may possibly be damaged. The method also has a problem in that strong autofluorescence of cells may affect the measurement. Moreover, the fluorescent triazole compound produced from 2,3-diaminonaphthalene does not necessarily have sufficient fluorescence intensity, and for this reason, it is difficult to accurately measure fluorescence in individual cells by using conventional fluorescence microscopes. There is also a problem in that 2,3-diaminonaphthalene itself has a relatively simple chemical structure and is not suitable as a fundamental structure for various chemical modification so as to be localized inside of cells.

The inventors of the present invention proposed two methods for measurement of nitric oxide that successively solve these problems.

One of the methods utilizes a diaminofluorescein derivative (hereafter also referred to as "DAF" in the specification, Japanese Patent Unexamined Publication (Kokai) No. 10-226688/1998). This method utilizing DAF is much excellent in reactivity with nitric oxide and measurement sensitivity. The method enables measurement of nitric oxide with excitation light of a long wavelength that does not damage living tissues and cells, and accurate measurement of nitric oxide existing in inside of cells for each individual cell, which are characteristic features of the aforementioned method. However, since a part of fluorescence wavelength range of the triazole derivatives (hereafter also referred to as "DAF-T") that are produced by the reaction of DAF with nitric oxide overlaps with the autofluorescence range of cells, the method may sometimes fail to accurately measure nitric oxide in certain types of samples. Further, since the fluorescence of DAF-T may be attenuated from weakly acidic to acidic region, a problem also arises in that accurate measurement over a wide pH range cannot be conducted.

The second method utilizes a diaminorhodamine derivative (hereafter also referred to as "DAR", International Patent Publication WO99/01447). This method is also based on the measurement of fluorescence of a triazole derivative (hereafter also referred to as "DAR-T") which is produced by the reaction of DAR with nitric oxide. The peak of the fluorescence spectrum of DAR-T lies around 580 nm (excitation wavelength: 565 nm), while the peak of the fluorescence spectrum of the aforementioned DAF-T is observed around 515 nm (excitation wavelength: 495 nm). Accordingly, measurements without being influenced by autofluorescence of cells can be performed by using DAR. Furthermore, since DAR-T can maintain a certain level or higher intensity of fluorescence in an acidic region as well as in a basic or a neutral region, it enables measurement of nitric oxide over a wide pH range. However, in the method utilizing DAR, fluorescence intensity of some DAR-T may sometimes slightly fluctuate depending on pH, and a problem arises that accurate measurement cannot be performed when a sample is measured whose pH is possibly fluctuate during measurement, e.g., a tissue of a patient with an ischemic disease. There is also a problem that DAR-T has lower fluorescence intensity as compared to the class of DAF-T.

DISCLOSURE OF THE INVENTION

An object of the present invention is to provide a compound useful for the measurement of nitric oxide. More specifically, the object is to provide a compound which has higher fluorescence intensity and whose fluorescent intensity is not fluctuated by pH, which compound is based on the aforementioned DAR that can maintain a certain level of fluorescence intensity in an acidic region as well as in a basic and a neutral region without being influenced by the autofluorescence. Another object of the present invention is to provide a reagent for measurement of nitric oxide comprising a compound having the aforementioned characteristics.

The inventors of the present invention conducted various researches to achieve the foregoing objects. As a result, they found that the rhodamine derivatives of the following structures readily reacted with nitric oxide in a sample for measurement to give triazole derivatives having high fluorescence intensity. They also found that the triazole derivatives had a substantially constant level of fluorescence intensity over a wide pH range from basic to acidic condition, and that their fluorescence intensities were improved. The present invention was achieved on the basis of these findings.

The present invention thus provides compounds represented by the following formula (I) or (II):

(I)

(II)

wherein, in the formula (I), $R^1$, $R^2$, $R^3$, and $R^4$ independently represent methyl group or ethyl group; and in the formula (II), $R^5$, $R^6$, $R^7$, and $R^8$ independently represent methyl group or ethyl group and $X^-$ represents an anion. According to preferred embodiments of the present invention, there are provided: the compounds of the formula (I) wherein $R^1$, $R^2$, $R^3$, and $R^4$ are ethyl groups; the compounds of the formula (I) wherein $R^1$, $R^2$, $R^3$, and $R^4$ are methyl groups; the compounds of the formula (II) wherein $R^5$, $R^6$, $R^7$, and $R^8$ are methyl groups; and the compounds of the formula (II) wherein $R^5$, $R^6$, $R^7$ and $R^8$ are methyl groups and $X^-$ is $I^-$. According to another aspect of the present invention, there are provided reagents for measurement of nitric oxide which comprises a compound represented by the aforementioned formula (I) or formula (II).

According to a further aspect of the present invention, there are provided compounds represented by the following formula (III) or (IV):

(III)

(IV)

wherein, in the formula (III), $R^{11}$, $R^{12}$, $R^{13}$, and $R^{14}$ independently represent methyl group or ethyl group; and in the formula (IV), $R^{15}$, $R^{16}$, $R^{17}$, and $R^{18}$ independently represent methyl group or ethyl group and $Y^-$ represents an anion. According to preferred embodiments of the aforementioned invention, there are provided: the compounds wherein $R^{11}$, $R^{12}$, $R^{13}$, and $R^{14}$ are ethyl groups; the compounds wherein $R^{11}$, $R^{12}$, $R^{13}$ and $R^{14}$ are methyl groups; the aforementioned compounds wherein $R^{15}$, $R^{16}$, $R^{17}$ and $R^{18}$ are methyl groups; and the aforementioned compounds wherein $R^{15}$, $R^{16}$, $R^{17}$ and $R^{18}$ are methyl groups and $Y^-$ is $I^-$.

According to a still further aspect of the present invention, there are provided methods for measurement of nitric oxide, which comprise step (1) in which a compound represented by the aforementioned formula (I) or (II) is reacted with nitric oxide, and step (2) in which a compound represented by the formula (III) or (IV) produced in the step (1) is detected.

BEST MODE FOR CARRYING OUT THE INVENTION

In the aforementioned formula (II), the kind of the anion represented by $X^-$ is not particularly limited. For example, halogen ions such as chlorine ion, bromine ion and iodine ion, inorganic ions such as sulfate ion, nitrate ion and perchlorate ion as well as organic acid ions such as methanesulfonate ion, p-toluenesulfonate ion, oxalate ion and citrate ion may be used. Preferably, iodine ion may be used.

In the formula (I), a compound wherein $R^1$, $R^2$, $R^3$, and $R^4$ all represent ethyl group, or wherein $R^1$, $R^2$, $R^3$, and $R^4$ all represent methyl group is preferred, and a compound wherein $R^1$, $R^2$, $R^3$, and $R^4$ all represent methyl group is particularly preferred. In the formula (II), a compound wherein $R^5$, $R^6$, $R^7$, and $R^8$ are methyl groups is preferred, and a compound wherein $R^5$, $R^6$, $R^7$, and $R^8$ are methyl groups and $X^-$ is $I^-$ is most preferred.

In the formula (III), a compound wherein $R^{11}$, $R^{12}$, $R^{13}$, and $R^{14}$ all represent ethyl group, or wherein $R^{11}$, $R^{12}$, $R^{13}$, and $R^{14}$ all represent methyl group is preferred, and a compound wherein $R^{11}$, $R^{12}$, $R^{13}$, and $R^{14}$ all represent methyl group is particularly preferred. In the formula (IV), a compound wherein $R^{15}$, $R^{16}$, $R^{17}$, and $R^{18}$ are methyl groups is preferred, and a compound wherein $R^{15}$, $R^{16}$, $R^{17}$, and $R^{18}$ are methyl groups and $Y^-$ is $I^-$ is most preferred.

Methods for preparing typical compounds falling within the compounds of the present invention will be shown in the following schemes. However, the methods for preparing the compounds of the present invention are not limited to the following methods (in the schemes, AM represents acetoxymethyl group, and DIEA represents diisopropylethylamine). It will be understood by those skilled in the art that any compounds represented by the formulas (I) and (II) or the formulas (III) and (IV) can readily be prepared by referring to the general explanation in the following schemes and specific description in the examples. The method for preparing diaminorhodamine is disclosed in WO99/01447 and a specific method for preparing DAR-1 is also described therein. Therefore, any compounds falling within the formulas (I) through (IV) can be readily prepared by combination of known preparation methods available to those skilled in the art, the methods disclosed in the above publication, and the methods described in the examples of the present specification.

The compounds of the present invention may exist as hydrates or solvates, and it should be understood that these substances also fall within the scope of the present invention. Furthermore, it is known that rhodamine derivatives may form a lactone ring and exist as compounds in a free form. It will be readily understood by those skilled in the art that the compounds of the present invention represented by the formulas (I) and (III) may exist in structural isomers forming the lactone ring. Those structural isomers also fall within the scope of the present invention (it will also be readily understood by those skilled in the art that a quaternary amino group does not exist in the aforementioned compounds). The compounds of the present invention forming a lactone ring are shown by the following formulas (I)' and (III)' (these compounds correspond to those represented by the formulas (I) and (III), respectively, and $R^1$ to $R^4$ and $R^{11}$ to $R^{14}$ have the same meanings as those defined above).

In the aforementioned formulas (I) and (III), as well as in the aforementioned schemes, only the compounds that do not form a lactone ring are shown for the sake of convenience. In these compounds, the positive charge on the quaternary amino group is neutralized by the carboxyl anion to form an intramolecular zwitterion. Therefore, they do not have an anion represented by $X^-$ or $Y^-$ that serves as a counter ion.

The compounds of the present invention represented by the formula (I) or (II) have a property that they efficiently react with nitric oxide under a neutral condition to give a compound of the formula (III) or (IV) in a good yield. The compounds represented by the formula (I) or (II) themselves do not emit substantial fluorescence when they are irradiated by excitation light at about 565 nm under a neutral condition, whilst the compounds of the formula (III) or (IV) emit extremely strong fluorescence under the same condition (emission: 580 nm). Therefore, nitric oxide in living tissues or cells can be measured by allowing the compounds represented by the formula (I) or (II) to be uptaken into the living tissues or cells and to react with nitric oxide to generate fluorescent compounds of the formula (III) or (IV), and then measuring fluorescence of the resulting compounds. The compounds of the formula (III) or (IV) produced as described above maintain substantially constant fluorescence intensity over a region of from weakly basic condition of about pH 9 to acidic condition of about pH 4, and they show more superior fluorescence intensity than that of DAR-1T or DAR-2T specifically disclosed in WO99/01447.

Therefore, the method for measuring nitric oxide provided by the present invention thus comprises steps of reacting a compound represented by the formula (I) or (II) with nitric oxide to form a compound of the formula (III) or (IV), respectively, and then measuring the fluorescence of the compound of the formula (III) or (IV). In the present specification, the term "measurement" should be construed in its broadest sense including measurement for various purposes such as detection, and quantitative or qualitative determinations. The aforementioned reaction can preferably be performed under a neutral condition, for example, within a range of pH 6.0 to 8.0, preferably pH 6.5 to 7.8, more preferably pH 6.8 to 7.6. However, the measurement of nitric oxide according to the present invention is not limited to measurement under a neutral condition. The fluorescence intensity of the compounds of the formula (III) or (IV) is constant over a wide pH range, and hence accurate measurement can be conducted even when measurement is performed for a sample in which pH fluctuation is expected during the measurement, for example, a tissue of a patient with an ischemic disease.

The compounds of the formula (II) readily pass through lipophilic cytoplasmic membranes and are uptaken into the cells, and then the ester is hydrolyzed to give compounds of the formula (I) having carboxyl group. Since the compounds of the formula (I) are highly hydrophilic, they are not easily excreted from the inside of the cells. Therefore, the compounds of the formula (II) per se are useful as an agent for the measurement.

The measurement of fluorescence can be performed by a known conventional fluorescence measuring method (see, for example, publications such as Wiersma, J. H., Anal. Lett., 3, pp.123–132, 1970; Sawicki, C. R., Anal. Lett., 4, pp.761–775, 1971; Damiani, P. and Burini, G., Talanta, 8, pp.649–652, 1986; Misko, T. P., Anal. Biochem. 214, pp.11–16, 1993 and so forth). In the method for measurement of nitric oxide according to the present invention, for example, it is preferred that light of about 565 nm is irradiated as excitation light, and fluorescence at about 580 nm is measured. By using lights having such wavelengths, efficient spectrometry can be performed by means of a fluorescence filter of an ordinarily used fluorescence microscope, and measurement with high sensitivity can be attained without using a special filter.

When particularly high sensitivity measurement is required, the measurement of nitric oxide may be performed in the presence of an oxygen source. As the oxygen source, for example, oxygen, ozone, oxide compounds and so forth may be used. Dissolved oxygen can generally be used as the oxygen source, and if necessary, oxygen gas may be introduced into a reaction system, or a reagent for generating oxygen (for example, hydrogen peroxide and the like) may be added. The oxide compounds are not particularly limited so long as they have an oxide bond from which oxygen atom is readily released, for example, N—O, S—O, and P—O. For example, PTIO (2-phenyl-4,4,5,5-tetramethylimidazoline-1-oxyl-3-oxide, Maeda, H., et al., J. Leuk. Biol., 56, pp.588–592, 1994; Akaike T., et al., Biochemistry, 32, pp.827–832, 1993) or its derivatives (carboxy-PTIO which is formed by introducing carboxyl group into the paraposition of the phenyl group of PTIO and the like), triphenylphosphine oxide, triethylamine oxide and so forth can be used.

Among the aforementioned oxide compounds, PTIO and its derivatives (for example, carboxy-PTIO and the like) are particularly preferred compounds, and they are readily obtained by those skilled in the art (listed in Tokyo Chemical Industry Co., Ltd., Organic Chemicals Catalog, 32, 1994 and so forth). The oxide compounds, per se, may be used as a reaction reagent, or those encapsulated in liposomes or similar materials can also be used. An amount of the oxygen source is not particularly limited, and the amount may preferably be at least about 1 μM or more, more preferably about 10 to 30 μM, and most preferably about 10 to 20 μM based on nitric oxide to be measured. In the measurement for biological samples and so forth, the oxygen source may preferably be added to a sample in an amount of about 10 to 20 μM. However, a necessary amount of the oxygen source may generally be supplied by dissolved oxygen. The reaction may be performed within a temperature range of 10 to 40° C.

EXAMPLES

The present invention will be more specifically explained with reference to the following examples. However, the scope of the present invention is not limited to the following examples. In the examples, the descriptions such as "DAR-4M" correspond to those of the compounds shown in the above schemes.

Example 1

Preparation of 3,6-bis(Diethylamino)-9-[3-amino-4-(N-methylamino)-2-carboxyphenyl]xanthylium Intramolecular Salt (DAR-M)

DAR-1 [3,6-bis(diethylamino)-9-[3,4-diamino-2-carboxyphenyl]xanthylium intramolecular salt] prepared by the method disclosed in WO99/01447 (231 mg) was dissolved in 10 ml of ethanol and added with 50 μl of methyl iodide (1.7 equivalents based on DAR-1), and the temperature of the reaction mixture was raised to 80° C. While the degrees of disappearance of the starting material and production of a dimethyl compound were observed for every hour using thin layer chromatography (TLC), the mixture was added with additional 50 μl of methyl iodide. The reaction was terminated when the desired compound was produced. The product was purified by silica gel column chromatography and preparative TLC to obtain the title compound (25 mg, 11%).

m.p. 150–154° C.; $^1$H-NMR (300 MHz, CDCl$_3$) δ 1.13 (12H, t, J=7.0), 2.86 (3H, s), 3.33 (8H, q, J=7.0), 6.37–6.43 (5H, m), 6.75 (1H, d, J=7.9), 6.81 (2H, d, J=9.0); FAB-MS 487 (M$^+$+1).

Example 2

Preparation of 3,6-bis(Diethylamino)-9-(4-carboxy-1-methylbenzotriazol-5-yl)xanthylium Intramolecular Salt (DAR-MT)

DAR-M (8.0 mg) obtained in Example 1 was dissolved in methanol and the solution was bubbled with nitric oxide, and then the solvent was evaporated. The residue was purified by preparative TLC to obtain DAR-MT.

m.p. 155–160° C.; $^1$H-NMR (300 MHz, CDCl$_3$) δ 1.12 (12H, t, J=7.1), 3.32 (8H, q, J=7.1), 4.37 (3H,s), 6.31 (2H, dd, J=9.0, 2.5), 6.43 (2H, d, J=2.5), 6.58 (2H, d, J=9.0), 7.26 (1H, d, J=8.6), 7,83(1H, d, J=8.6); FAB-MS 498 (M$^+$+1).

Example 3

Preparation of 3,6-bis(Dimethylamino)-9-[3-amino-4-(N-methylamino)-2-carboxyphenyl]xanthylium Intramolecular Salt (DAR-4M)

In the same manner as in Example 1, the title compound was obtained (140 mg, 24.5%) from 553 mg of DAR-4 [3,6-bis(dimethylamino)-9-[3,4-diamino-2-carboxy-phenyl]xanthylium intramolecular salt] which was prepared by the method disclosed in WO99/01447.

m.p. 219° C.; $^1$H-NMR (300 MHz, CDCl$_3$) δ 2.92 (3H, s), 2.97 (12H, s), 4.99 (2H, br), 6.40 (2H, dd, J=8.6, 2.6), 6.47 (2H, d, J=2.6), 6.47 (2H, d, J=8.0), 6.75 (2H, d, J=8.6), 6.85 (1H, d, J=8.0); FAB-MS 431 (M$^+$+1).

Example 4

Preparation of 3,6-bis(Dimethylamino)-9-(4-carboxy-1-methylbenzotriazol-5-yl)xanthylium Intramolecular Salt (DAR-4MT)

In the same manner as in Example 2, the title compound was obtained (18.5 mg, 72%) from DAR-4M (25 mg) obtained in Example 3.

m.p. 242–245° C.; $^1$H-NMR (300 MHz, CDCl$_3$) δ 2.98 (12H, s), 4.41 (3H, s), 6.36 (2H, dd, J=9.0, 2.6), 6.50 (2H, d, J=2.6), 6.62 (2H, d, J=9.0), 7.24 (1H, d, J=8.5), 7.77 (1H, d, J=8.5); FAB-MS 442 (M$^+$+1).

Example 5

Preparation of 3,6-bis(Dimethylamino)-9-[2-acetoxymethoxycarbonyl-3-amino-4-(N-methylamino)phenyl]xanthylium Iodide (DAR-4M AM)

3,6-Bis(dimethylamino)-9-(3-amino-2-carboxy-4-nitrophenyl)xanthylium intramolecular salt (2.44 g) prepared by the method disclosed in WO99/01447 was dissolved in 120 ml of dichloroethane, and the solution was added with 1 ml of diisopropylethylamine. The mixture was further added with acetoxymethyl bromide (0.55 ml), and stirred at room temperature. The progress of the reaction was monitored every day by TLC, and additional diisopropylethylamine and acetoxymethyl bromide were added in amounts half of those used for the first addition. After 4 days, the reaction mixture was added with dichloroethane and washed with water, and the solvent was evaporated. The residue was purified by silica gel column chromatography to obtain 3,6-bis(dimethylamino)-9-(2-acetoxymethoxycarbonyl-3-amino-4-nitrophenyl) xanthylium bromide (0.445 g, 13.6%).

$^1$H-NMR (300 MHz, CDCl$_3$) δ 1.75 (3H, s), 3.40 (12H, s), 5.41 (2H, s), 6.56 (1H, d, J=8.6), 6.97 (2H, d, J=2.4), 7.07 (2H, dd, J=9.5, 2.4), 7.18 (2H, d, J=9.5), 8.45 (2H, br), 8.54(1H, d, J=8.6).

The aforementioned 3,6-bis(dimethylamino)-9-(2-acetoxymethoxycarbonyl-3-amino-4-nitrophenyl) xanthylium bromide (443 mg) was dissolved in a mixed solvent of ethanol (100 ml) and dichloromethane (100 ml), and the solution was added with 0.25 g of 10% Pd/C catalyst. The mixture was stirred at room temperature under a hydrogen atmosphere for 2 hours. The reaction mixture was filtered, and the solvent was evaporated. The residue was purified by silica gel column chromatography to obtain 3,6-bis(dimethylamino)-9-(2-acetoxymethoxycarbonyl-3,4-diaminophenyl)xanthylium bromide (214 mg, 50.9%).

$^1$H-NMR (300 MHz, CDCl$_3$) δ 1.69 (3H, s), 3.33 (12H, s), 4.81 (2H, br), 5.32 (2H, s), 6.29 (1H, d, J=7.9), 6.47 (2H, br), 6.78 (2H, d, J=2.6), 6.91 (2H, dd, J=9.5, 2.6), 6.94 (2H, d, J=7.9), 7.45 (2H, d, J=9.5).

From the above 3,6-bis(dimethylamino)-9-(2-acetoxymethoxycarbonyl-3,4-diaminophenyl)xanthylium bromide (133 mg), 3,6-bis(dimethylamino)-9-[2-acetoxymethoxycarbonyl-3-amino-4-(N-methylamino)phenyl]xanthylium iodide was obtained (40.5 mg, 27.5%) in the same manner as in Example 1.

m.p. 177–178° C.; $^1$H-NMR (300 MHz, CDCl$_3$) δ 1.69 (3H, s), 2.99 (2H, d, J=4.6), 3.36 (12H, s), 5.06 (1H, q, J=4.6), 5.33 (2H, s), 6.34 (2H, s), 6.46 (1H, d, J=7.9), 6.69 (1H, d, J=7.9), 6.79 (2H, d, J=2.6), 6.91 (2H, dd, J=9.5, 2.6), 7.48 (2H, d, J=9.5); FAB-MS 503 (M$^+$).

Example 6

Preparation of 3,6-bis(Diethylamino)-9-[2-acetoxymethoxycarbonyl-3-amino-4-(N-methylamino)phenyl]xanthylium Iodide (DAR-M AM)

In the same manner as in Example 5, the title compound was obtained from 3,6-bis(diethylamino)-9-(3-amino-2-carboxy-4-nitrophenyl)xanthylium intramolecular salt which was prepared by the method disclosed in WO99/01447.

m.p. 147–150° C.; $^1$H-NMR (300 MHz, CDCl$_3$) δ 1.34 (12H, t, J=7.0), 1.67 (3H, s), 2.98 (3H, s), 3.63 (8H, q, J=7.0), 5.36 (2H, s), 6.42 (1H, d, J=8.0), 6.66 (1H, d, J=8.0), 6.75 (2H, d, J=2.4), 6.84 (2H, dd, J=9.3, 2.4), 7.43 (2H, d, J=9.3); FAB-MS 559 (M$^+$).

Example 7

Figure 1:
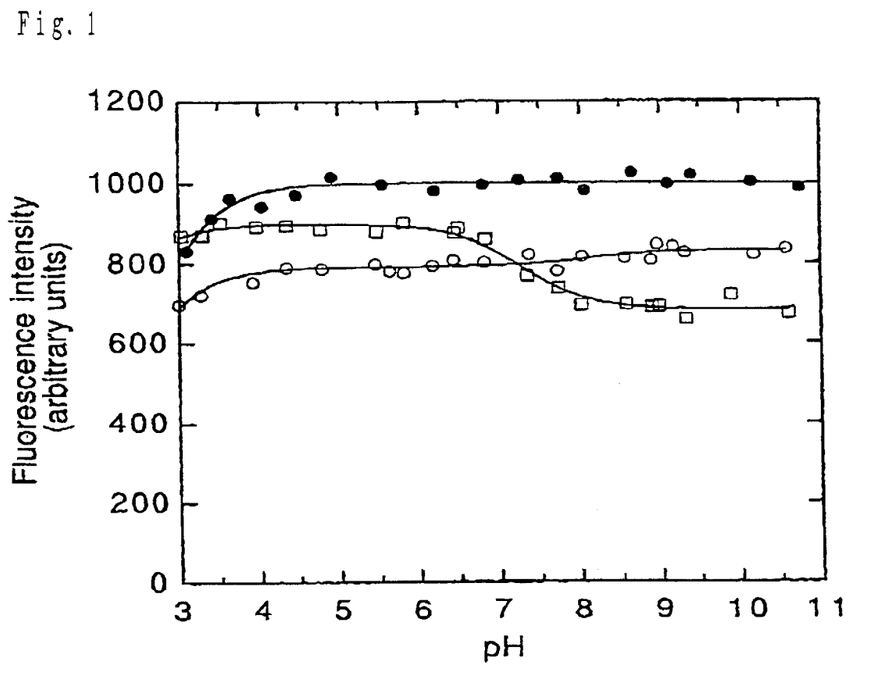
FIG. 1 shows change in fluorescence intensity of a compound of the present invention (DAR-MT) and DAR-1T and DAR-2T disclosed in WO99/01447 with pH fluctuation. In the figure, ○ indicates the results for DAR-1T, ☐ for DAR-2T, and ● for DAR-MT.

Change in Fluorescence Intensity of the Compounds of the Present Invention by pH Fluctuation The triazole derivatives DAR-1T and DAR-2T prepared by the method disclosed in WO99/01447 and DAR-MT prepared in Example 2 were each dissolved at 1 μM in 0.1 M sodium phosphate buffer prepared at various pHs, and fluorescence intensity of each sample was measured. The excitation wavelength/emission wavelength were as follows: DAR-1T; 565/580, DAR-2T; 565/575 and DAR-MT; 565/575 (nm). The results are shown in FIG. 1. In the figure, ○ indicates the results for DAR-1T, ☐ for DAR-2T, and ● for DAR-MT. DAR-MT of the present invention was found to have constant fluorescence intensity in the range of pH from 4 to 11.

Figure 2:
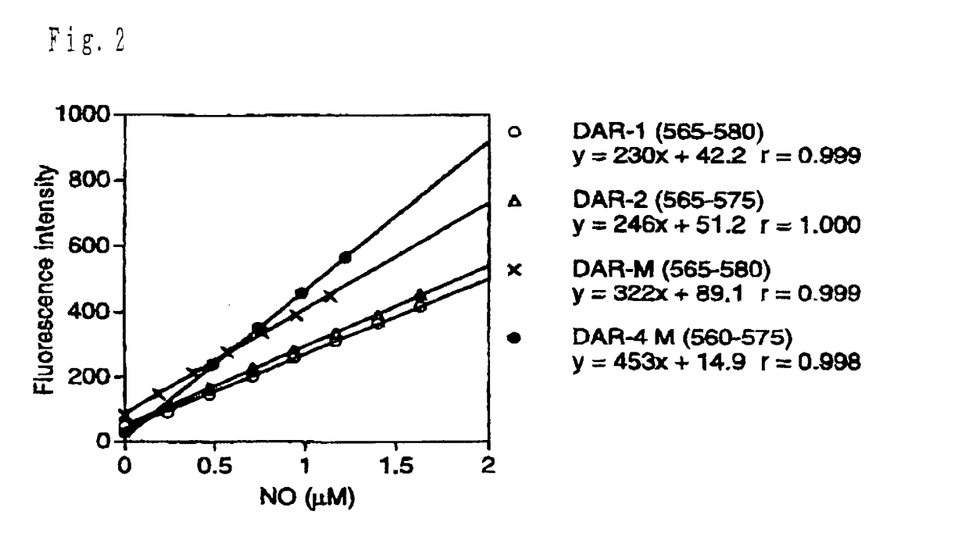
FIG. 2 shows change in fluorescence intensity with change in nitric oxide concentration measured by using compounds of the present invention (DAR-M and DAR-4M) and the compounds disclosed in WO99/01447 (DAR-1 and DAR-2). In the figure, ○ indicates the results for DAR-1, Δ for DAR-2, X for DAR-M, and ● for DAR-4M.

Nitric oxide was measured by using DAR-M obtained in Example 1 and DAR-4M obtained in Example 3. For comparison of measurement sensitivity, DAR-1 and DAR-2 disclosed in WO99/01447 were used as reference compounds. Each compound was dissolved at 10 μM in 0.1 M sodium phosphate buffer at 37° C. The solution was added with nitric oxide, and change in fluorescence intensity with variation of nitric oxide concentration was measured. The nitric oxide used was prepared by bubbling nitric oxide in 0.1 M sodium phosphate buffer (pH 7.4) after argon substitution, and measured by the HRP method (Kikuchi, K. et al., Biol. Pharm. Bull., 19, pp. 649–651, 1996). Excitation wavelength/emission wavelength were as follows: DAR-1; 565/580, DAR-2; 565/575, DAR-M; 565/580 and DAR-4M; 560/575 (nm). The results of sensitivity comparison using a calibration curve are shown in FIG. 2. In the figure, ○ indicates the results for DAR-1, Δ for DAR-2, X for DAR-M, and ● for DAR-4M. DAR-M and DAR-4M of the present invention were found to have 1.4 to 1.7 times higher sensitivity than DAR-1 and DAR-2.

Example 9

Imaging of Nitric Oxide in Cells

Figure 3:
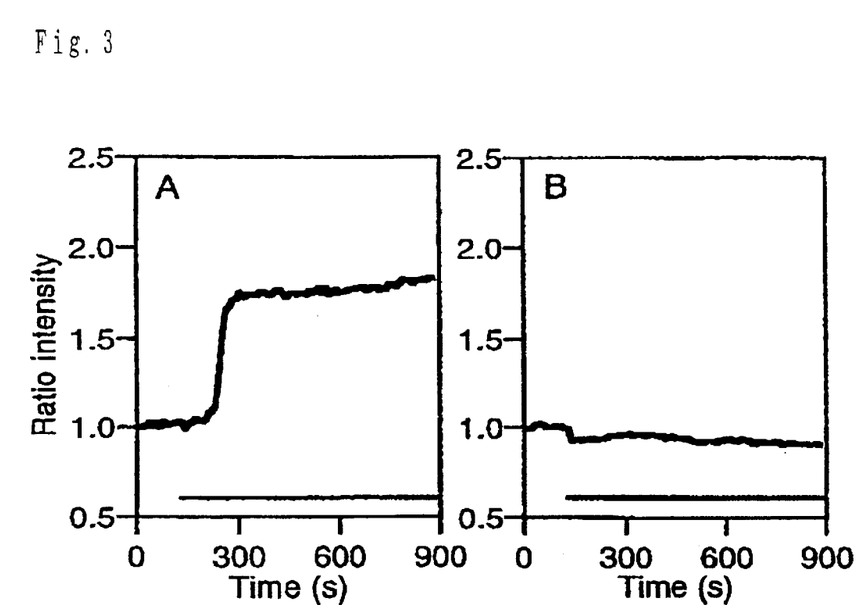
FIG. 3 shows results of imaging of intracellular nitric oxide performed by using a compound of the present invention (DAR-4M AM). The results are shown with averaged change in relative fluorescence intensity of arbitrary seven cells based on the fluorescence intensity at the time of the start of the measurement. In the figure, (a) shows that the fluorescence intensity was increased by stimulation with bradykinin, and (b) shows that the fluorescence intensity was not increased in the presence of a nitric oxide synthetase inhibitor (1 mM L-NAME).

Bovine aorta endothelial cells were cultured on an imaging dish. The culture broth was changed to DMEM medium (supplemented with 0.2% DMSO) containing DAR-4M AM (10 μM) prepared in Example 5, and incubated at 37° C. for 30 minutes to load DAR-4M AM on the cells. The cells were washed, and the culture broth was changed again to DMEM medium not containing DAR-4M AM. After incubation at 37° C. for 1 hour, imaging was performed. The cells were examined with a fluorescence microscope equipped with an excitation filter (520 to 550 nm), a dichromic mirror (565 nm), and a barrier filter (580 nm, long pass). The measurement was performed in a warm box kept at 37° C. Imaging interval was set to be 10 seconds, and images captured by a cooled charge-coupled device camera were recorded and analyzed by an image analyzer. The results are shown in FIG. 3. The results in the figure are shown with averaged change of relative fluorescence intensity of arbitrary seven cells based on the fluorescence intensity at the time of the start of the measurement. The fluorescence intensity was increased by stimulation with bradykinin (FIG. 3(A)), but the fluorescence intensity was not increased in the presence of a nitric oxide synthetase inhibitor (1 mM L-NAME) (FIG. 3(B)). These results clearly indicate that DAR-4M AM was taken into the cells, and DAR-4M produced in the cells specifically reacted with nitric oxide in the cells. These results demonstrate that intracellular nitric oxide can be specifically measured with high sensitivity at individual cell.

INDUSTRIAL APPLICABILITY

The compounds of the present invention are useful as reagents for measurement of nitric oxide. The compounds of the formula (I) or (II) of the present invention have a property to efficiently react with nitric oxide to give fluorescent compounds of the formula (III) or (IV). The compounds of the formula (III) or (IV) are characterized in that (1) they have high fluorescence intensity, (2) they are not influenced by autofluorescence, and (3) they have no fluorescence intensity fluctuation over a wide pH range. It is known that intracellular pH may fluctuate when endothelial cells are stimulated by bradykinin (Fleming, I., et al., Cir. Res., 74, pp.1220–1226, 1994). In particular, said compounds are featured by successful accurate measurement of nitric oxide when a sample with expected pH fluctuation is measured.

What is claimed is:

1. A compound represented by the following formula (I) or (II):

(II)

wherein, in the formula (I), $R^1$, $R^2$, $R^3$, and $R^4$ independently represent methyl group or ethyl group; and in the formula (II), $R^5$, $R^6$, $R^7$, and $R^8$ independently represent methyl group or ethyl group and $X^-$ represents an anion.

2. The compound of the formula (I) according to claim 1, wherein $R^1$, $R^2$, $R^3$, and $R^4$ are methyl groups.

3. The compound of the formula (II) according to claim 1, wherein $R^5$, $R^6$, $R^7$, and $R^8$ are methyl groups and $X^-$ is $I^-$.

4. A reagent for measurement of nitric oxide which comprises a compound represented by the formula (I) or formula (II) according to claim 1.

5. A compound represented by the following formula (III) or (IV):

(III)

(IV)

wherein, in the formula (III), $R^{11}$, $R^{12}$, $R^{13}$, and $R^{14}$ independently represent methyl group or ethyl group; and in the formula (IV), $R^{15}$, $R^{16}$, $R^{17}$, and $R^{18}$ independently represent methyl group or ethyl group and $Y^-$ represents an anion.

6. The compound of the formula (III) according to claim 5, wherein $R^{11}$, $R^{12}$, $R^{13}$, and $R^{14}$ are methyl groups.

7. The compound of the formula (IV) according to claim 5, wherein $R^{15}$, $R^{16}$, $R^{17}$, and $R^{18}$ are methyl groups and $Y^-$ is $I^-$.

8. A method for measurement of nitric oxide, which comprises:

(1) a step of reacting a compound represented by the formula (I) or (II) according to claim 1 with nitric oxide, and (2) a step of detecting a compound represented by the formula (III) or (IV) produced in the step (1).

* * * * *